US012606852B2

(12) United States Patent
Johnson et al.

(10) Patent No.: US 12,606,852 B2
(45) Date of Patent: Apr. 21, 2026

(54) CONVERSION OF LIGNIN-DERIVED MONOMERS TO MUCONATE BY ENGINEERED PSEUDOMONAS

(71) Applicant: Alliance for Sustainable Energy, LLC, Golden, CO (US)

(72) Inventors: Christopher W. Johnson, Denver, CO (US); Gregg Tyler Beckham, Golden, CO (US); Allison Jean Zimont Werner, Denver, CO (US)

(73) Assignee: Alliance for Energy Innovation, LLC, Golden, CO (US)

( * ) Notice: Subject to any disclaimer, the term of this patent is extended or adjusted under 35 U.S.C. 154(b) by 0 days.

(21) Appl. No.: 17/691,075

(22) Filed: Mar. 9, 2022

(65) Prior Publication Data

US 2022/0290193 A1 Sep. 15, 2022

Related U.S. Application Data

(60) Provisional application No. 63/158,845, filed on Mar. 9, 2021.

(51) Int. Cl.
| | |
|---|---|
| *C12P 7/44* | (2006.01) |
| *C12N 9/02* | (2006.01) |
| *C12N 15/52* | (2006.01) |
| *C12N 15/63* | (2006.01) |
| *C12P 7/42* | (2006.01) |

(52) U.S. Cl.
CPC .............. *C12P 7/42* (2013.01); *C12N 9/0036* (2013.01); *C12N 15/52* (2013.01); *C12N 15/63* (2013.01)

(58) Field of Classification Search
CPC ......... C12P 7/42; C12N 9/0036; C12N 15/52; C12N 15/63
See application file for complete search history.

(56) References Cited

U.S. PATENT DOCUMENTS

2017/0275655 A1* 9/2017 Beckham ....... C12Y 401/01077

FOREIGN PATENT DOCUMENTS

JP 2010268773 A * 12/2010

OTHER PUBLICATIONS

Jha, Ramesh K., et al. "A protocatechuate biosensor for Pseudomonas putida KT2440 via promoter and protein evolution." Metabolic engineering communications 6 (2018): 33-38 (Year: 2018).*
PubChem, compound summary, 3- oxohexanedioic acid, 2024, www.pubchem.ncbi.nlm.nih.gov/compound/3-Oxoadipic-acid (Year: 2024).*
Appendix A sequence alignment (Year: 2024).*

(Continued)

*Primary Examiner* — Thane Underdahl
*Assistant Examiner* — Mary A Crum
(74) *Attorney, Agent, or Firm* — Sam J. Barkley

(57) ABSTRACT

Disclosed herein are engineered *Pseudomonas* useful to relieve the metabolic bottleneck of 4-hydroxybenzoate transformation in a muconate accumulating strain on an engineered *Pseudomonas* by swapping its endogenous para-hydroxybenzoate-3-hydroxylase (PHBH), PobA, with a homolog, PraI, that has a broader cofactor preference.

4 Claims, 6 Drawing Sheets

Specification includes a Sequence Listing.

(56) References Cited

OTHER PUBLICATIONS

Clarkson et al., "Construction and Optimization of a Heterologous Pathway for Protocatechuate Catabolismin *Escherichia coli* Enables Bioconversion of Model Aromatic Compounds", Applied and Environmental Microbiology, 2017, vol. 83, No. 18, pp. 1-13.

Kasai et al., "Uncovering the protocatechuate 2,3-cleavage pathway genes", Journal of Bacteriology, 2009, vol. 191, No. 21, pp. 6758-6768.

Kuatsjah et al., "Debottlenecking 4-hydroxybenzoate hydroxylation in Pseudomonas putidaKT2440 improves muconate productivity from p-coumarate", Metabolic Engineering, 2022, vol. 70, pp. 31-42.

* cited by examiner

A                    B                    C

SEQUENCE LISTING

```
<160> NUMBER OF SEQ ID NOS: 3

<210> SEQ ID NO 1
<211> LENGTH: 1188
<212> TYPE: DNA
<213> ORGANISM: Artificial Sequence
<220> FEATURE:
<223> OTHER INFORMATION: The pobA (PP_3537) sequence from P. putida
      KT2440 codon optimized for expression in E. coli used for the
      constructions of pEUK005 and pEUK018.

<400> SEQUENCE: 1
atgaagacgc aggttgcaat tatcggcgca ggtccgagcg gcctccttct gggtcaattg       60
ctgcataaag cgggcattga taatattatt gtggaacgcc agactgcgga atatgtcctg      120
ggccgcatcc gtgcaggtgt gctggagcag ggtaccgtgg atctgctgcg ggaagcgggt      180
gtagcggaac gcatggatcg ggaagggtta gtgcacgaag gggtagagct gctggtgggc      240
ggacgtcgtc agcgtctcga cctgaaagcg ctgactggag gcaagacggt catggtctat      300
ggtcaaacgg aggtcacccg cgatctgatg caggcccgcg aagcatcagg tgcgccgatc      360
atctacagcg cggcaaacgt tcagccacac gagctgaagg gagaaaagcc atacttgacg      420
ttcgaaaaag atggtcgcgt ccagcgcatt gattgcgatt atattgcggg atgcgatggc      480
ttccatggta tctcgcgtca gagtatcccg gaaggtgttc tgaagcagta tgagcgtgtc      540
```

-continued

```
tatccgtttg gttggttggg gctgttaagc gacacaccgc ccgttaacca tgaactgatc      600
tacgcacacc atgaacgcgg tttcgctctt tgcagccagc gttcgcagac ccgttcacgc      660
tactacctgc aggtcccatt gcaggatcgt gttgaagaat ggtccgacga acgtttctgg      720
gatgaattga aagcccgcct gcctgcggaa gttgcggcgg acctggttac gggaccggcg      780
ttggaaaaaa gcattgcccc attgcgcagc ctggtggtgg aaccaatgca gtacggtcac      840
ctgttcttag tgggtgatgc ggcgcacatt gtgccgccga ccggcgccaa aggcctgaat      900
ctggccgcga gcgatgttaa ttatctgtat cgtattctgg ttaaagttta ccacgaaggt      960
cgggtggacc tgttggccca gtatagcccg ctggcgctgc gccgcgtgtg aaaggagaa      1020 cgttttagct ggttcatgac gcaactttta cacgactttg ggagccataa agatgcgtgg      1080
gatcagaaga tgcaggaagc cgaccgggag tattttctga cgtcgccggc gggtctggtg      1140
aacattgctg aaaactacgt tggcttaccg ttcgaagaag tggcctga                  1188
```

<210> SEQ ID NO 2
<211> LENGTH: 1179
<212> TYPE: DNA
<213> ORGANISM: Artificial Sequence
<220> FEATURE:
<223> OTHER INFORMATION: The praI (BAH79107) sequence from Paenibacillus
     JJ-1b codon optimized for expression in E. coli used for the
     construction of pEE003.

<400> SEQUENCE: 2

```
cgcacccagg ttggtatcat tggcgcgggt ccggccggtc tgttgctgtc ccacttgctg       60
tacctgcagg gcatcgaaag catcatcatc gaaaaccgta cccgtgagga aatcgaaggt      120
acgattcgtg ccggtgtact ggaacagggc accgttgatc tgatgaatca gatgggggtg      180
ggcgcgcgta tgatgaagga gggccacttc acgaaaggtt cgaactgcg cttcaacggt       240 cgtggccacc gtatcaacgt acacgagctg accggtggta aatacgtcac ggtttatgcc      300
cagcacgaag ttattaaaga cctcgtggct gcacgtctgc aaacaggtgg tcagattcat      360
tttaacgtag gtgacgttag cctgcacgac gttgatacca gctctccgaa aatccgtttt      420
cgcccgaaca aagacggtga gctgcaggag attgaatgcg acttcatcgc gggttgcgat      480
ggtttccgtg gcccgtcacg cccggcaatc ccacagtccg tacgtaaaga ataccaaaaa      540
gtgtatcctt tcagctggct gggcatcctc gtggaggcgc cgccgtccgc tcacgaactg      600
atctacgcga accatgaacg tggttttgca ctggtgagta cccgctcacc gcagattcag      660
cgtctgtacc tgcaggtaga cgcgcaggat catattgaca actggtctga tgaccgtatc      720
tggagcgaac tccacgcgcg cctggaaact cgtgatggtt tcaaactgct ggaaggcccg      780
atcttccaaa agggtatcgt ttccatgcgc agcttcgtat gtgatccaat gcagcacggt      840
cgcctgttcc tagcaggtga tgcggcgcac atcgtaccgc cgaccggcgc caaaggtctg      900
aacctggcag cggccgacgt tcaggtcctg gccgtgtggt tagaagcata ttacaaagct      960
ggcaaaatgg aaattctgaa ccgctgcacc gaaatttgcc tccgtcgtat ctggaaagcc     1020
gaacgcttca gctggttcat gactactatg ctccaccgtg accagggcca tactccgttc     1080
gaacgcggta tccaactggc agagctggac tatgttacct cttctcgtgc cgcgtcaacc     1140
agcctggctg aaaactatat tggcctgccg atggagttc                            1179
```

<210> SEQ ID NO 3
<211> LENGTH: 1185
<212> TYPE: DNA
<213> ORGANISM: Artificial Sequence -continued

```
<220> FEATURE:
<223> OTHER INFORMATION: The praI (BAH79107) sequence from Paenibacillus
      JJ-1b codon optimized for expression in E. coli used for the
      constructions of pEUK006 and pEUK019.

<400> SEQUENCE: 3
atgcgcactc aggtaggcat tattggggcc ggtccggctg ggttgctgtt gtcacatttg      60
ttatatttgc aagggatcga aagcatcatt attgagaacc gtacgcgtga ggagattgag     120
ggtaccattc gcgcaggtgt gttagaacag ggcacggtgg atctgatgaa tcaaatgggt     180
gtgggtgccc gtatgatgaa agaaggccac ttccacgaag ggtttgagct ccgttttaac     240
ggccgcgggc atcgtatcaa tgtgcacgag ctgacgggtg gcaaatacgt tacggtgtac     300
gcgcaacatg aggttatcaa agatctggtt gcggcgcgcc tgcagaccgg cgggcaaatt     360
cattttaacg ttggtgacgt aagcttacac gacgtcgata cctctagccc gaaaattcgt     420
tttcgtccca ataaagatgg cgaactgcaa gaaattgagt gcgacttcat cgccggttgc     480
gacggctttc gcgggccgtc tcgcccggca atcccgcaga gtgtacgtaa agaatatcag     540
aaggtttatc cttttagctg gttaggcatt ctggtcgaag cgccgccttc tgcgcatgaa     600
cttatttatg caaatcatga gcggggtttt gcactggtgt cgacgcgctc accgcaaatt     660
caacggcttt acttacaggt ggacgcccaa gatcatatcg acaactggag cgacgaccgc     720
atctggagtg aattgcacgc gcgccttgaa actcgggacg gcttcaagct gctggaggga     780
ccgatctttc aaaaaggtat tgtttccatg cggtcatttg tgtgcgatcc gatgcaacat     840
ggtcgtttat ttctggctgg cgatgctgcc catatcgtgc ccccgactgg ggcgaaaggt     900
cttaacctgg ccgctgcaga cgtccaagtc cttgcgcgtg gcctggaagc gtattataaa     960
gccggcaaga tggaaattct gaaccgttgc accgaaatct gcttacgccg catctggaag    1020
gctgagcgct ttagttggtt catgactacc atgctgcatc gcgatcaggg acacacccct    1080
ttcgaacgtg gtatccagct cgcggaactg gattacgtaa cctcttcgcg cgcggcgtcg    1140
acgagcctcg ccgaaaacta tatcggcttg ccgatggagt tttga                    1185
```

CONVERSION OF LIGNIN-DERIVED MONOMERS TO MUCONATE BY ENGINEERED PSEUDOMONAS

CROSS-REFERENCE TO RELATED APPLICATIONS

This application claims priority under 35 U.S.C. § 119 to U.S. provisional patent application No. 63/158,845 filed on 9 Mar. 2021, the contents of which are hereby incorporated in their entirety.

CONTRACTUAL ORIGIN

The United States Government has rights in this invention under Contract No. DE-AC36-08GO28308 between the United States Department of Energy and the Alliance for Sustainable Energy, LLC, the Manager and Operator of the National Renewable Energy Laboratory.

SEQUENCE LISTING

This application contains a Sequence Listing which has been submitted via EFS-web and is hereby incorporated by reference in its entirety. The ASCII copy as filed herewith was originally created on 21 Feb. 2022. The ASCII copy as filed herewith is named NREL_20-28_Sequence_listing_ST25.txt, is 5744 bytes in size and is submitted with the instant application.

BACKGROUND

An efficient lignin utilization is key for a competitive biomass-based economy to facilitate the transition away from the current fossil-fuel based counterpart due to the latter's impending scarcity and adverse contribution towards climate change.

*Pseudomonas putida* KT2440 (*P. putida*, hereafter) is a versatile biological funneling chassis that enables the conversion of heterogenous feedstock chemicals such as lignin-related aromatics and sugars into a consolidated panel of higher-value products. *P. putida* hosts wide ranging inherent aromatic catabolic pathways in conjunction to robust genetic tools to lend itself for use in industrial processes. The catabolic repertoire of *P. putida* can be readily expanded to by genetic integration of exogenous pathways; for example, the introduction of lsdE and lsdA from Novosphingobium *aromaticivorans* DSM12444 allow *P. putida* to catabolize 1,2-diguaiacyl-propane-1,3-diol (DGPD), a lignin-related β-1 dimer that is unaffected by WT *P. putida*.

Integrated genetic engineering and bioprocess optimization approaches have enabled *P. putida* to transform p-coumarate and ferulate to muconate with a near unity of carbon balance.

Nevertheless, the productivity is still below industrially relevant levels which is due in part to the inefficiencies in several metabolic steps including the hydroxylation of 4-hydroxybenzoate (4HB) to protocatechuate (PCA).

Para-hydroxybenzoate-3-hydroxylase (PHBH) catalyzes the hydroxylation of p-hydroxybenzoate (4HB) to protocatechuate (PCA). Decades of research has greatly scrutinized the molecular mechanism of PHBH, most notably those from *Pseudomonas aeruginosa* & *Pseudomonas fluorescens*, and established this enzyme as a paradigm for flavoprotein oxygenases.

SUMMARY

In an aspect, disclosed herein are engineered *Pseudomonas* useful to relieve the metabolic bottleneck of 4-hydroxybenzoate transformation in an engineered *Pseudomonas* by swapping its endogenous para-hydroxybenzoate-3-hydroxylase (PHBH), PobA, with PraI. In an embodiment, the engineered *Pseudomonas* is capable of increased production of muconic acid from p-coumarate when compared to a non-engineered *Pseudomonas*. In an embodiment, the engineered *Pseudomonas* is capable of producing 40 g/L of muconic acid. In an embodiment, the engineered *Pseudomonas* of has a gene encoding for PraI is greater than 70% identical to SEQ ID NO: 2. In an embodiment, the engineered *Pseudomonas* has a gene encoding for PraI is greater than 70% identical to SEQ ID NO: 3. In an embodiment, the engineered *Pseudomonas* is *Pseudomonas* strain CJ781.

In an aspect, disclosed herein is an engineered *Pseudomonas* useful to relieve the metabolic bottleneck of 4-hydroxybenzoate transformation in an engineered *Pseudomonas* comprising PraI. In an embodiment, the engineered *Pseudomonas* is capable of increased production of muconic acid from p-coumarate when compared to a non-engineered *Pseudomonas*. In an embodiment, the engineered *Pseudomonas* is capable of producing 40 g/L of muconic acid. In an embodiment, the engineered *Pseudomonas* has a gene encoding for PraI that is greater than 70% identical to SEQ ID NO: 2. In an embodiment, the engineered *Pseudomonas* has a gene encoding for PraI is greater than 70% identical to SEQ ID NO: 3.

In an aspect, disclosed herein is an engineered *Pseudomonas* capable of production of beta-ketoadipic acid useful to relieve the metabolic bottleneck of 4-hydroxybenzoate transformation in the engineered *Pseudomonas* comprising PraI. In an embodiment, the engineered *Pseudomonas* has a gene encoding for PraI is greater than 70% identical to SEQ ID NO: 2. In an embodiment, the engineered *Pseudomonas* has a gene encoding for PraI is greater than 70% identical to SEQ ID NO: 3. In an embodiment, the engineered *Pseudomonas* has a gene encoding for PraI is greater than 70% identical to SEQ ID NO: 2. In an embodiment, the engineered *Pseudomonas* is *Pseudomonas* strain AW271. In an embodiment, the engineered *Pseudomonas* is capable of increased production of muconic acid from p-coumarate when compared to a non-engineered *Pseudomonas*. In an embodiment, the engineered *Pseudomonas* has an endogenous para-hydroxybenzoate-3-hydroxylase (PHBH), PobA that is replaced with PraI.

Other objects, advantages, and novel features of the present invention will become apparent from the following detailed description of the invention when considered in conjunction with the accompanying drawings.

DESCRIPTION OF THE DRAWINGS

FIG. 1A depicts CJ475 (expressing pobA only), FIG. 1B depicts CJ680 (expressing pobA and praI), or FIG. 1C depicts CJ781 (expressing praI only) cultivated in M9 minimal media containing 20 mM pCA and 10 mM glucose with an additional 10 mM glucose fed at 12, 24, and 48 h. Samples were taken periodically to measure growth and metabolite concentrations.

Error bars represent the standard deviation across biological triplicates each with technical duplicates.

Figures 3A, 3B, 3C:
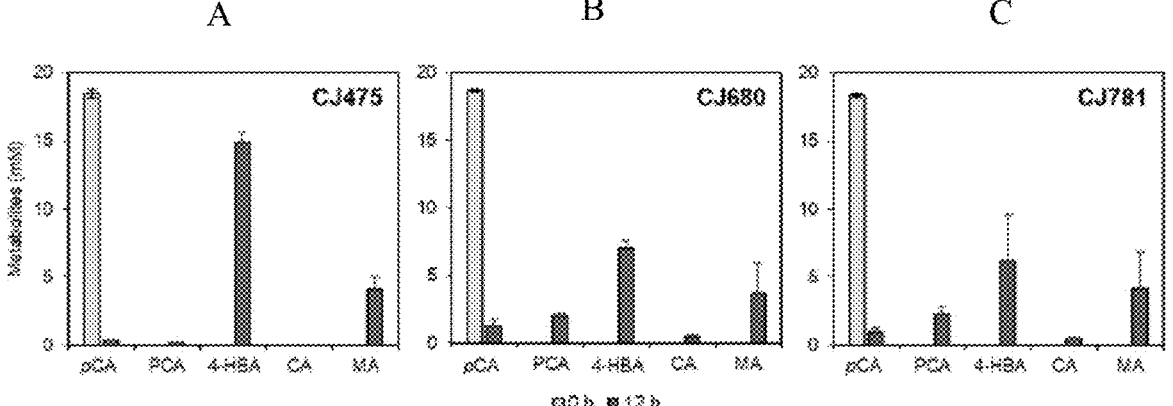

FIGS. 3A, 3B and 3C depict feed, intermediate, and product concentrations in shake flasks corresponding to the NADP+/NADPH assays and protein quantification at 12 hours of cultivation. FIG. 3A depicts CJ475, FIG. 3B depicts CJ680, and FIG. 3C depicts CJ781 cultivations in shake flasks with M9 minimal medium supplemented with 20 mM glucose and ~20 mM pCA. pCA, p-coumarate; PCA, protocatechuate; 4-HBA, 4-hydroxybenzoate; CA, catechol; MA, muconate.

Figure 4:
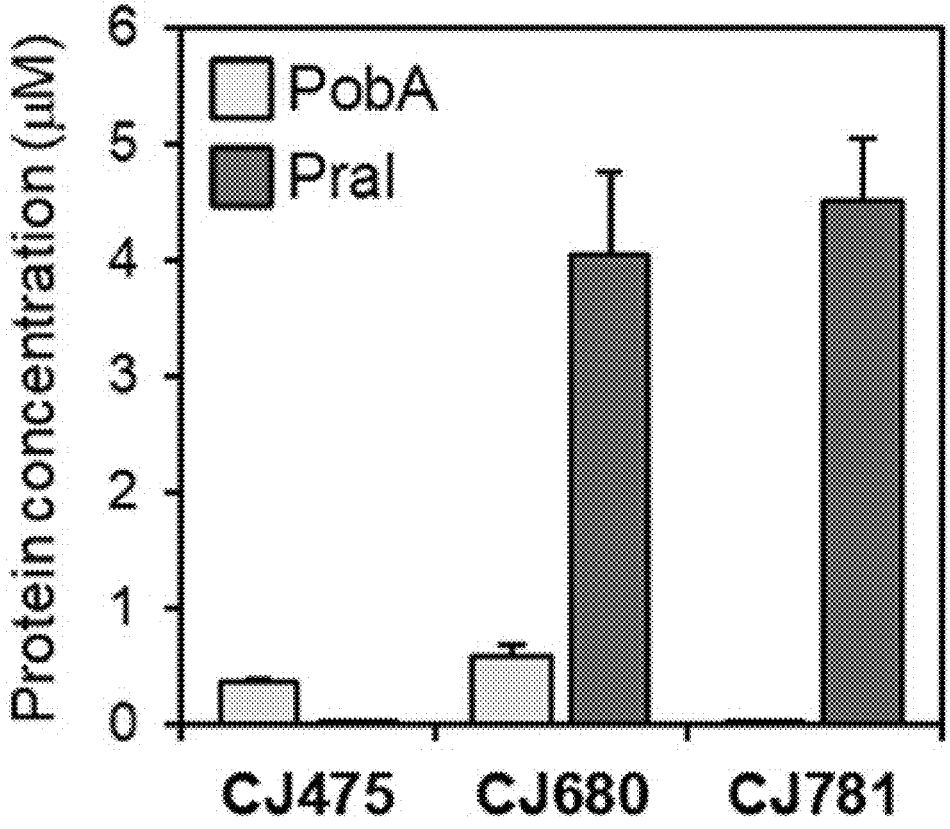

FIG. 4 depicts PobA and PraI abundance in *P. putida* strains CJ475, CJ680, and CJ781 after 12 hours of cultivation in M9 minimal medium supplemented with 20 mM glucose. Strain genotypes are provided in Table 5. Four and five unique validated labeled peptides were used for PobA and PraI measurements, respectively. Error bars represent the standard deviation across biological triplicates.

FIGS. 5A, 5B, 5C, 5D, 5E and 5F depict bioreactor cultivations with CJ475, CJ680, and CJ781. pCA was fed at two different initial feeding rates in the fed-batch phase: (FIGS. 5 A-C) at 6 mmol/h and (FIGS. 5 D-F) at 9 mmol/h. Bacterial growth ($OD_{600}$), metabolite profiles, and MA titers (T), yields (Y), and productivities (P) are shown for each case. The asterisks indicate the time point at which T, Y, and P were calculated (either before pCA accumulated in the bioreactors or when the feeding was depleted). Profiles shown are the average of biological duplicates (excluding FIG. 5D, which is a single cultivation). Error bars show the absolute difference between the biological duplicates.

Figures 6A, 6B, 6C, 6D:
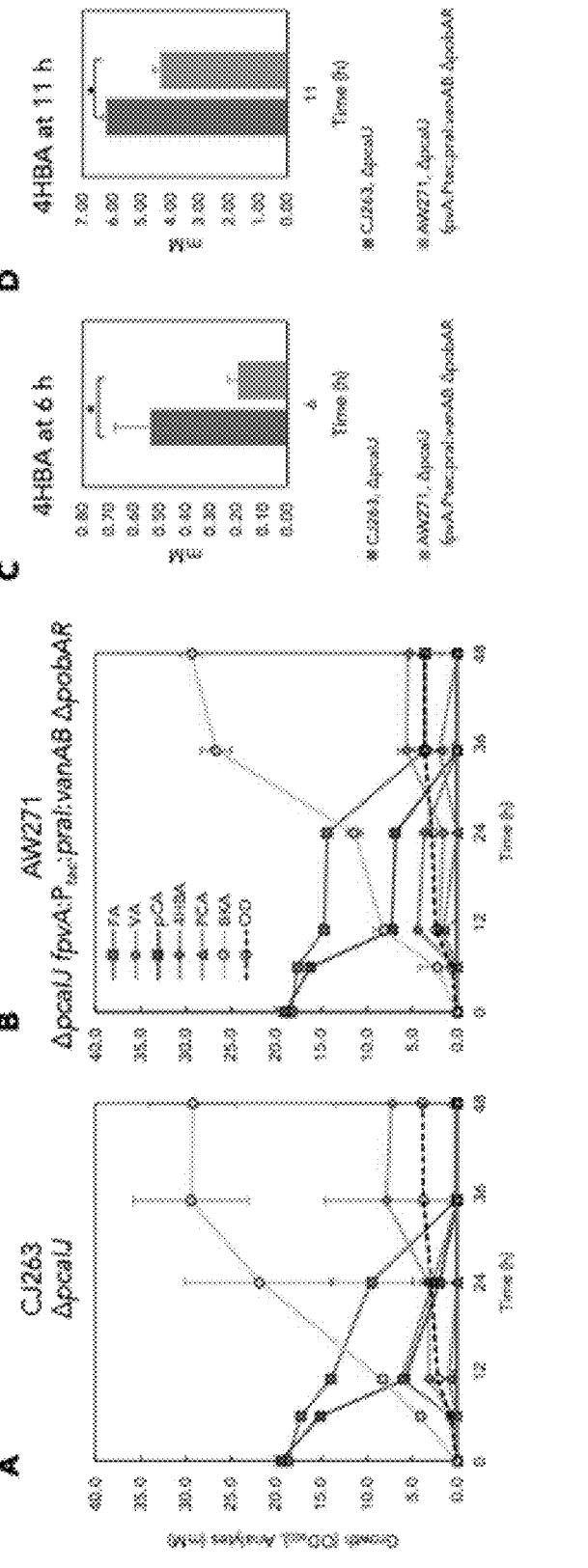

FIGS. 6A, 6B, 6C, and 6D depict substrate, intermediate, and product concentrations and cell growth (optical density at 600 nm) that were measured over time (FIGS. 6 A-B). Notably, 4-hydroxybenzoate accumulation was significantly reduced at both 6 h and 11 h of cultivation in AW271 as compared to CJ263 ($p<0.05$, paired one-tailed t-test, FIGS. 6 C-D).

DETAILED DESCRIPTION

The transformation of 4-hydroxybenzoate (4HB) to protocatechuate (PCA) is a step in microbial aerobic catabolism of aromatic compounds and catalyzed by flavoprotein oxygenases colloquially known as para-hydroxybenzoate-3-hydroxylase (PHBH). In *Pseudomonas putida* KT2440 strains engineered to convert various lignin-derived aromatic monomers to the platform chemical, muconic acid (MA), the activity of PHBH is a known rate-limiting step as indicated by the accumulation of 4HB in the culture milieu, which subsequently limits the MA titer and productivity from reaching an industrially relevant level. Disclosed herein are methods and compositions to replace the native NADPH-specific PHBH, PobA, with PraI, a PHBH from *Paenibacillus* sp. JJ-1b which can utilize both NADH and NADPH. This replacement reduces the accumulation of 4HB and consequently improve the strain's overall performance. This substitution also boosts the bioavailability of intra-cellular NADPH while minimally affecting the NADH level.

In an optimized bioreactor cultivation, the PraI-bearing strain exhibits an improved tolerance towards the aromatics. Further, the final MA titer improved and was achieved faster compared to its PobA-bearing counterpart. In-vitro kinetic assays unexpectedly found that both PobA and PraI can utilize NADPH at a comparable substrate specificity; in addition, PraI can also efficiently utilize NADH albeit at a slightly lowered specificity (about 60%).

Structurally, the two enzymes are virtually identical and the differential NAD(P)H preference is attributed to transient interactions with a flexible loop as previously described. Thus, disclosed herein are non-naturally occurring *Pseudomonas putida* KT2440 useful as a biocatalyst that embody the benefit of sampling readily available natural enzyme diversity for enabling a more efficient metabolic flux in strain engineering.

In an embodiment, disclosed herein are engineered *Pseudomonas* engineered for heterologous expression of a 4-hydroxybenzoate 3-hydroxylase to improve 4-hydroxybenzoate metabolism.

The gene encoding the p-hydroxybenzoate hydroxylase (4-hydroxybenzoate 3-monooxygenase) from *Paenibacillus* sp. JJ-1b was heterologously expressed in *Pseudomonas putida* to improve metabolism of 4-hydroxybenzoate in this host.

During conversion of p-coumarate, a product of lignin deconstruction, to the polymer precursor muconic acid in *P. putida* KT2440, a metabolic intermediate, 4-hydroxybenzoate, was found to accumulate, and indicated that activity of the native 4-hydroxybenzoate hydroxylase, PobA, was limiting the rate of conversion. To overcome this, we first attempted to overexpress PobA, but this was unsuccessful. We then tried heterologous expression of PraI, a 4-hydroxybenzoate hydroxylase from *Paenibacillus* sp. JJ-1b by integrating a gene encoding this enzyme into the genome of our muconate production strain. Heterologous expression of PraI dramatically reduced the accumulation of 4-hydroxybenzoate and, subsequently, increased the productivity of the resulting strain. Thus, in an embodiment, this solution may be useful in situations when availability of NADPH is limiting but NADH is available, since PraI can accept NADH or NADPH while PobA accepts only NADPH.

PraI Substitution Alleviates 4HB & PCA Accumulation

Figures 1A, 1B, 1C:
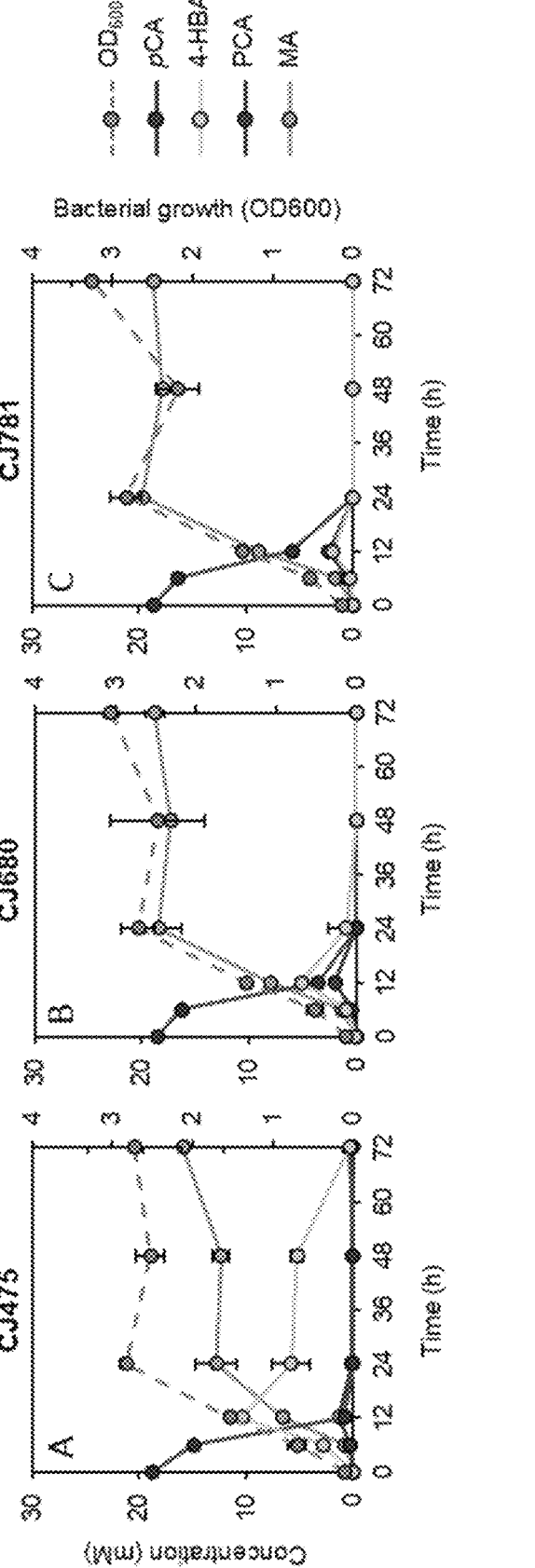
FIGS. 1A, 1B, and 1C depict shake flask cultivations of *P. putida* engineered for pCA conversion to MA via the intermediate 4-HBA.

In our initial engineered strain, KT2440-CJ475, 4-HBA accumulates to ~50% of the feed (FIG. 1A). To alleviate the 4-HBA bottleneck, PraI was overexpressed in KT2440-CJ680. In shake flasks, we saw close to a 50% reduction in 4-HBA accumulation at 12 hours. In an effort to further mitigate this bottleneck, pobA was deleted from CJ680. In KT2440-CJ781 the 4-HBA bottleneck was significantly reduced. PraI alone was more beneficial than co-expression of PobA and PraI. We hypothesized differences in performance of PraI and PobA could be attributed to differences in cofactor specificity.

Thus, in an embodiment, PraI substitution reduces 4-HBA accumulation during pCA conversion to MA Previously, we engineered *P. putida* to convert pCA and FA to MA generating strain CJ475 (FIG. 1A, Table 5). However, CJ475 accumulated up to −10 mM 4-HBA at 12 hours of cultivation in shake flask experiments fed with 20 mM pCA and 10 mM glucose, with an additional 10 mM glucose added after 12, 24, and 48 hours to support growth (FIG. 1A). A previous attempt to address this bottleneck by integrating a second copy of pobA, driven by the strong, constitutive tac promoter (Ptac), was not successful, so we next explored whether expression of praI might improve 4-HBA conversion. To do this, praI was integrated into the genome in the same locus where the second copy of pobA had been in CJ475, namely downstream of the Ptac and upstream of a second copy of vanAB, which encodes the native vanillate O-demethylase that was overexpressed in CJ475 to overcome vanillate accumulation. The resulting strain (CJ680, Table 5) exhibited a 50% reduction in 4-HBA accumulation at 12 hours of cultivation in shake flasks (FIG. 1B), indicating that the introduction of praI led to a faster conversion of 4-HBA and improved the rate of MA production. To ascertain the relative contributions of PobA and PraI, pobA was deleted from CJ680, generating strain CJ781. Fortunately, CJ781 showed a further reduction in 4-HBA accumulation (FIG. 1C), indicating that expression of PraI alone enabled faster 4-HBA conversion to PCA. Applicants deposited engineered *Pseudomonas putida* strains CJ781 and AW271 into the international depositary authority at the Agricultural Research Service Culture Collection (NRRL) located at 1815 North University Street, Peoria, Illinois 61604 in order to satisfy the requirements for the furnishing of samples according to 37 CFR 1.808 under the rules for microorganism deposit under the Budapest Treaty on the international recognition of the deposit of microorganisms for the purposes of patent procedure (Budapest Treaty). a depository (e.g. ATCC) so that the public may have access to the claimed strains. The NRRL accession numbers for the 10 Sep. 2024 accession date deposit of Applicant's engineered *Pseudomonas putida* strains AW271 and CJ781 are, respectively, B-68427 and B-68428.

PraI Substitution Improves the Intracellular NADPH Pool for Other Cellular Processes To understand the relative contributions of PobA and PraI to the 4-HBA hydroxylase activity, we evaluated the cofactor concentrations at $t_{12}$. In an embodiment, in CJ475 and CJ680, both of which express PobA, no NADPH was detected but it represented about 25% of the total NADP+/NADPH pool in CJ781, which expresses only PraI (FIG. 2). This is consistent with the observation that PobA accepts only NADPH while PraI is capable of using either NADPH or NADH. In addition to 4-HBA hydroxylase activity, NADPH is required by many other reactions and processes within the cell and these data suggest that CJ475 and CJ680 could be impaired by the limited availability of NADPH caused by PobA.

We sought to further understand the underlying cause for 4-HBA accumulation differences observed in CJ475, CJ680, and CJ781 in vivo. Considering PobA and PraI have different cofactor specificity (Table 1)—notably, that PobA requires NADPH whereas PraI accepts NADH and NADPH—we hypothesized that 4-HBA turnover in PobA-expressing strains may be limited by NADPH availability. To test this, we measured intracellular NADP+ to NADPH ratios (NADP+/NADPH) in CJ475, CJ680, and CJ781. NADP+/NADPH was measured at 12 hours of shake flask cultivation in M9 minimal medium supplemented with 10 mM glucose and 20 mM pCA (FIG. 2). This timepoint was chosen as the strain was in an exponential growth phase and 4-HBA accumulation is maximal of the sampled timepoints (FIG. 2).

Figures 2A, 2B:
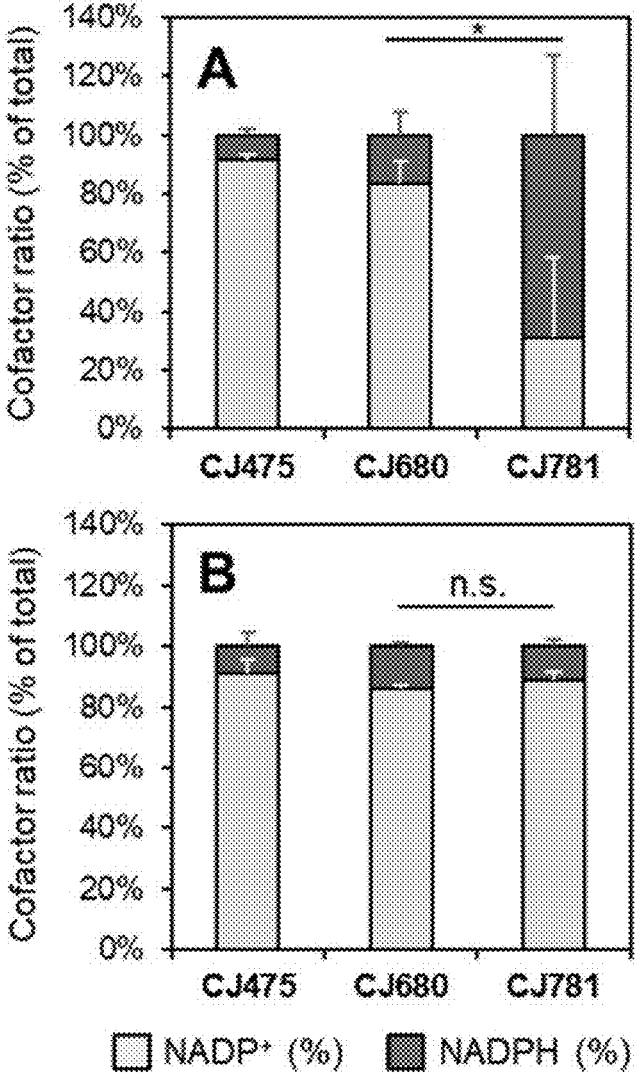
FIGS. 2A, and 2B depict the percentage of the NADP(H) pool represented by NADP+ and NADPH in *P. putida* strains CJ475, CJ680, and CJ781. Measurements were performed at 12 hours of cultivation in M9 minimal medium supplemented with (FIG. 2A) 20 mM pCA and 10 mM glucose or (FIG. 2B) 10 mM glucose. NADP+ and NADPH are presented as a percentage of the total NADP(H) pool.

In CJ475 and CJ680 cultivations, NADPH represented 9±2% and 17±8% of the total NADP(H) pool (FIG. 2A). Conversely, in CJ781 cultivations, NADPH represented 70±30% of the total NAD(P)H pool, a significantly higher proportion relative to CJ680 (p<0.05, paired one-tailed t-test, FIG. 2A). NADP+/NADPH ratios of 10±3, 6±5, and 0.5±0.7 were observed for CJ475, CJ680, and CJ781, respectively. The elevation in NADPH observed in CJ781 is consistent with elevated NADPH production in *P. putida* strains grown in the presence of aromatic substrates. A higher NADP+/NADPH, indicative of lower NADPH availability, in CJ475 and CJ680 is consistent with the hypothesis that PobA-mediated 4-HBA hydroxylation was limited by NADPH. However, NADPH is required by many other cellular processes in addition to PHBH activity, so we considered whether the genetic background of a given strain, as opposed to PobA activity alone, could underpin these results. In cultivations with only glucose, NADP+/NADPH was similar across all three strains (FIG. 2B): NADPH (% of total) was 9±4%, 14±1%, and 11±3% in CJ475, CJ680, and CJ781, respectively. Moreover, 4-HBA bottlenecks observed in CJ475 and CJ680 are attributable to NADP+/NADPH imbalance, and thereby limited PHBH activity. Overall, the presence of PobA is detrimental as it competes for a futile 4-HBA transformation in CJ680 due to NADPH limitation.

PraI is Highly Overexpressed Compared to PobA

We considered whether simply low PraI expression could be the reason for a lower NADP+/NADPH ratio during pCA conversion to MA, as opposed to more balanced nicotinamide utilization during 4-HBA hydroxylation. PobA is expressed via native genetic elements in CJ475 and CJ680, whereas praI is expressed via the Ptac and a synthetic ribosome binding site (RBS) in CJ680 and CJ781. However, a prior study involving heterologous expression of praI in a non-native host observed poor translation rates stemming from the formation of hairpin loops near the RBS. Thus, we sought to quantify intracellular PobA and PraI abundances in CJ475, CJ680, and CJ781. Each protein was quantified at 12 hours, the same time point that cofactor ratios were measured. Four and five unique labeled peptides were validated for quantitation of PobA and PraI, respectively, and added to extracted protein samples at a known abundance to enable absolute quantitation. PobA was expressed in CJ475 and CJ680 only when pCA was present (FIG. 4). Interestingly, 6-fold more PraI than PobA was present in CJ680 cultivations in pCA and glucose (0.6±0.1 and 4±0.7 M PobA and PraI, respectively, FIG. 4). A similar level of PraI was detected in pCA-containing cultivations of CJ781 (4.5±0.5 µM) compared to CJ680 (p=0.28). This result confirms that overexpression of PraI in *P. putida* was achieved, and further suggests that the increased relative NADPH availability in CJ781 is due to the absence of PobA rather than low expression of praI.

Substitution of PobA with PraI Significantly Improves MA Productivity

Strain evaluation was next conducted in bioreactors to examine the effect of PraI expression on MA production in process relevant conditions, where differences in strain performance are often amplified. The bioreactor setup initially involves a batch phase in which the cells are grown on glucose and induced with pCA. The fed-batch phase initiation was coupled to the depletion of glucose at which point, this triggered the addition of a concentrated alkaline solution of pCA, glucose, and $(NH_4)_2SO_4$ (pH 9). To determine the appropriate feeding rate, we considered our shake flask experiment above and our previous work with *P. putida* CJ242 (which is equivalent to CJ475 without an additional copy of vanAB) where an increased pCA feed rates led to an accumulation of 4-HBA in CJ475, which indicates a metabolic bottleneck. Based on these observations, we selected initial feeding rates of 6 and 9 mmol of pCA per hour to monitor the bottleneck in the 4-HBA conversion.

Figures 5A, 5B, 5C, 5D, 5E, 5F:
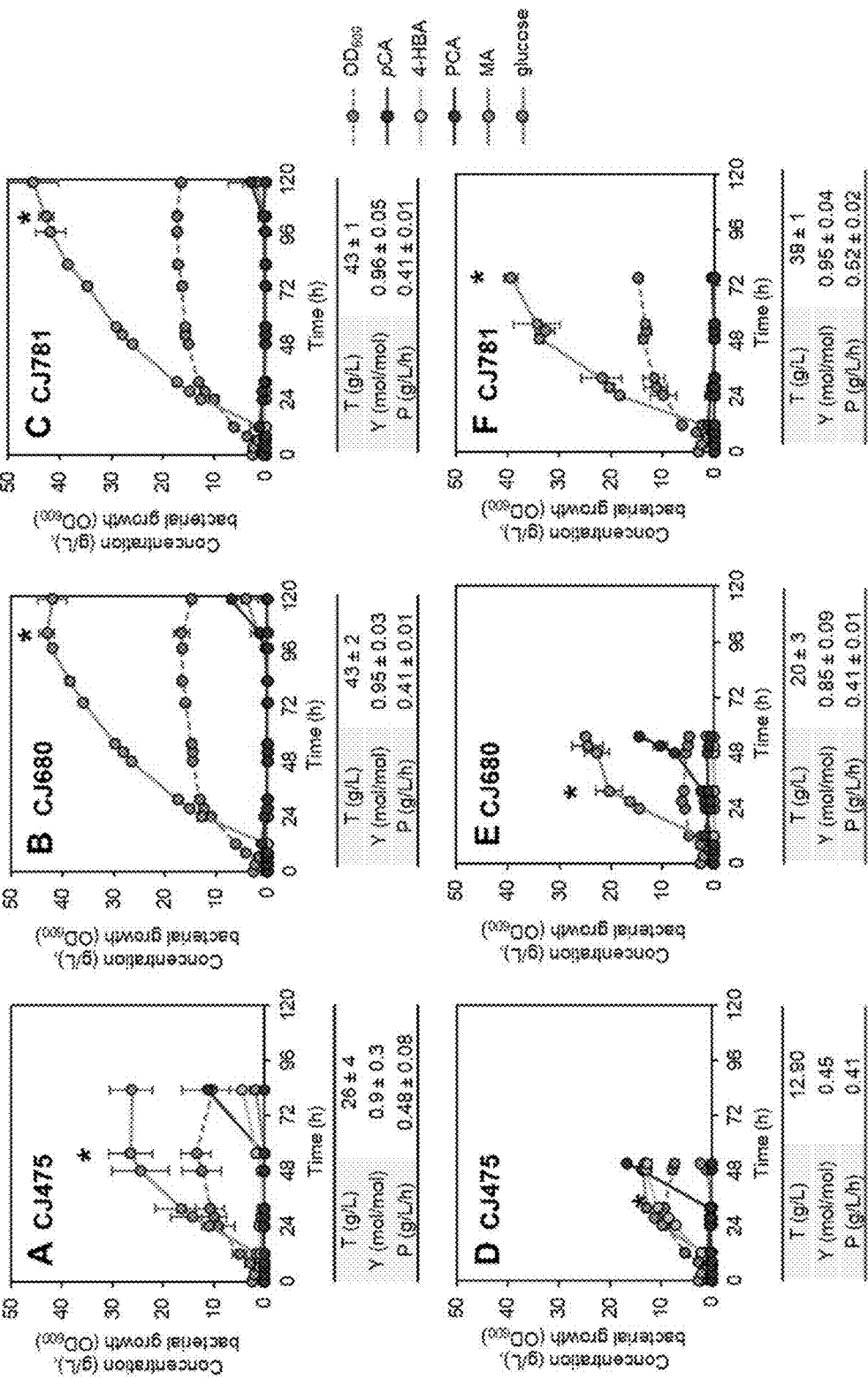

With a feed of 6 mmol pCA per hour, CJ475 accumulated 4-HBA whereas CJ680 and CJ781 did not, which enabled an increased MA titer of 43 g/L while maintaining a 0.95-0.96 mol/mol yield for both strains (FIGS. 5A-C). To further enhance MA productivity, we increased feeding rates to 9 mmol of pCA per hour. 4-HBA accumulated in CJ475 when the feeding started (FIG. 5D), similar to our previous results with CJ242. Conversely, 4-HBA did not accumulate in either CJ680 or CJ781 cultivations (FIGS. 5E and F). Despite overcoming the 4-HBA bottleneck, the strain performance of CJ680 and CJ781 exhibited notable differences. Specifically, while CJ680 accumulated pCA early in the cultivation (~24 h) (FIG. 5E), CJ781 did not accumulate any pCA or any other catabolic intermediate, enabling a higher MA titer and productivity (FIG. 5F) than both CJ680 at 9 mmol/h (FIG. 5E) and CJ781 at 6 mmol/h (FIG. 5C). Based on these results, we continued evaluating the effect of higher feeding rates (12 and 15 mmol pCA per hour) on MA production in CJ781. pCA accumulated in the bioreactors as soon as the feeding initiated at both feeding rates which suggests the presence of an additional bottleneck likely related to pCA transport. Also, PCA (one of the most toxic aromatic catabolic intermediates in this pathway) accumulated up to 2.4 g/L which may represent an additional bottleneck upon the improvement of pCA transport.

Producing Beta-Ketoadipic Acid Using Strains Engineered with PraI

In an embodiment, replacing PobA with PraI is useful toward improving conversion of p-coumarate to β-ketoadipate. *Pseudomonas putida* KT2440 was engineered to produce beta-ketoadipic acid by deletion of pcaIJ. The resulting strain was named CJ263 (genotype: *P. putida* KT2440 ΔpcaIJ). To improve conversion of 4-hydroxybenzoate to protocatechuate, pobA, encoding the native para-hydrozy-benzoate-3-hydroxylase, and the pobR regulator were deleted, and the heterologous praI was constitutively over-expressed from the fpvA locus with the tac promoter along with vanAB, the native vanillate monooxygenase. The resulting strain was named AW271 (genotype: *P. putida* KT2440 ΔpcaIJ fpvA:Ptac.praI:vanAB ΔpobAR). CJ263 and AW271 were cultivated in M9 minimal medium supplemented with 20 mM glucose and an equimolar mixture of p-coumarate and ferulate each at 20 mM concentrations; glucose was fed to 20 mM every 24 h. Substrate, intermediate, and product concentrations and cell growth (optical density at 600 nm) were measured over time (FIGS. 6 A-B). Notably, 4-hydroxybenzoate accumulation was significantly reduced at both 6 h and 11 h of cultivation in AW271 as compared to CJ263 (p<0.05, paired one-tailed t-test, FIGS. 6 C-D). This data demonstrates that replacing pobA with praI reduces 4-hydroxybenzoate accumulation in strains engineered for beta-ketoadipic acid production from lignin-related aromatics.

PobA and PraI Efficiently Hydroxylates 4HB with Near Unity Coupling

The reaction stoichiometry, defined in this study as the molar equivalencies between the consumptions of 4HB, NAD(PH), and molecular oxygen, and the production of PCA, were confirmed in an oxygraph, spectrophotometric, and HPLC-based assays. Both PobA and PraI have a near unity stoichiometry for all the associated reaction components (Table 6). In accordance with this tight coupling, the turnover number (kcat) for PobA and PraI are consistent when the three co-substrates were varied individually (vide infra).

PobA and PraI efficiently hydroxylates 4HB with comparable specificities.

PHBH activity assay is typically performed spectroscopically by monitoring the depletion of the reduced nicotinamide during turnover. This assay takes advantage of the stark differential absorbance elicited by the reduced nicotinamide at 340 nm which is abolished when the cofactor is oxidized. Alternatively, the enzymatic activity can be monitored via the consumption of molecular oxygen upon its incorporation to 4HB. While the flavin reduction step, and the concurrent oxidation of NAD(P)H, precedes the oxygen activation step, the observed rates from the two assay methods should be comparable under the steady-state condition.

The in-vitro activity assay confirmed the nicotinamide cofactor preference for PobA and PraI. The addition of NADPH, but not NADH, elicited oxygen consumption in a mixture containing PobA and 4HB. PobA, like PHBH *P. aeruginosa* and PHBH *P. fluorescens*, only accept NADPH as the sole source of reducing equivalent and is unreactive toward NADH. By contrast, PraI can utilize both NADH and NADPH as reducing equivalents as described previously. In a mixture containing PraI and 4HB, the addition of either NADPH or NADH resulted in oxygen consumption.

A diminished enzymatic activity and substrate inhibition kinetics were observed when the assays are conducted in a buffer containing NaCl, consistent with the inhibitory effect of chloride ion towards PHBH activity. Subsequently, PHBH kinetic assays were performed in Tris/SO$_4$ pH 8 where PobA and PraI obey the Michaelis-Menten kinetics and no substrate inhibition are observed; moreover, this buffer was previously used and thus eases the comparison to the kinetic parameters established for other PHBHs. Unlike the native host, the heterologous expression system may lack the appropriate chaperones and accessory proteins which may ultimately lower the overall enzymatic activity. Further, heterologous expression systems typically use a strong promoter which triggers a vast accumulation of the target protein to an amount at times beyond the capacity of the host to supply the requisite cofactors. To account for a potentially lowered cofactor occupancy in the heterologously produced enzymes, the kinetic buffer was supplemented with FAD. The steady-state kinetic analyses are summarized in Table 1. The comparison between the two assay methods showed systematically lower $K_M$ values obtained using the spectroscopic methods. This slight bias may reflect the higher sensitivity and response rate of the instruments used. Additionally, an open cuvette was used in the spectrophotometric assays, in contrast to a sealed cuvette configuration used in the oxygraph assays as to prevent passive diffusion of O$_2$ with the atmosphere. The overall steady-state kinetic parameters agree with the established norm in PHBH whereby the $K_M$ values are ordered incrementally in the following fashion: 4HB, NAD(P)H, and O$_2$. This ordering is consistent with the proposed catalytic mechanism where 4HB binding improves the rate of FAD reduction by NAD(P)H for the subsequent O$_2$ activation. Evaluation of the $K_M$ of the O$_2$ implies that the kinetic parameters obtained with respect to 4HB and NAD(P)H are apparent values as they were tested using air-saturated buffer (about 3-4×$K_M$); however, equivalent $k_{cat}$ values obtained under various O$_2$, 4HB, and NAD(P)H concentrations suggests that the reported numbers are likely close to the true $K_M$ values.

The steady-state kinetic parameters disclosed herein are comparable to reported values for other PHBHs. More specifically, the parameters for the heterologously produced PobA are similar to the natively produced PHBHs from *P. aeruginosa* ($k_{cat}=63$ s$^{-1}$; $K_M^{4HB}=11$ μM; $K_M^{NADPH}=23$ μM; $K_M^{oxygen}=37$ μM) and *P. fluorescens* ($k_{cat}=55$ s$^{-1}$; $K_M^{4HB}=25$ μM; $K_M^{NADPH}=50$ μM). Both PobA and PraI have similar substrate specificities towards NADPH and the differences average ≤two-fold change under the different combination of the reactants. Comparing the substrate specificities of PraI towards the two forms of reducing equivalents indicated a slight preference towards NADPH; however, this observation is in contrast a prior description of an apparent preference of PraI towards NADH.

Table 1 discloses steady-state kinetic parameters of PobA and PraI as determined using methods and compositions disclosed herein. Experiments were performed using 50 mM Tris/SO$_4$, pH 8 supplemented with 60 µM FAD, at 25° C. Parameters were calculated using a minimum of 25 data points using Leonora. The experiments were performed using 200 µM 4-HBA, 300 µM NAD(P)H, and air-saturated buffer unless that the concentration of that substrate was varied. In an embodiment, two detection methods were used by monitoring the loss of NAD(P)H signal at 340 nm and using an oxygraph following the depletion of O$_2$.

a direct aromatic liquor as extracted from biomass while still maintaining high titer and yield.

Material & Methods

Co-factor quantifications. NAD$^+$/NADH (Catalog Number MAK037) and NADP$^+$/NADPH (Catalog Number MAK038) Colorimetric Assay kits from Sigma-Aldrich were used to determine ratio of oxidized to reduced co-factor in a sample. The kits were specific for either NAD$^+$/NADH or NADP$^+$/NADPH. The manufacturer's procedure was followed for data collection and final ratio calculations.

TABLE 1

| | | substrates | | | | | | | | | |
|---|---|---|---|---|---|---|---|---|---|---|---|
| | | O$_2$$^b$ | | | 4-hydroxybenzoate$^c$ | | | NAD(P)H$^d$ | | | |
| reducing equivalent | enzyme | k$_{cat}$ s$^{-1}$ | K$_M$ µM | k$_{cat}$/K$_M$ × 10$^5$ s$^{-1}$ · M$^{-1}$ | k$_{cat}$ s$^{-1}$ | K$_M$ µM | k$_{cat}$/K$_M$ × 10$^5$ s$^{-1}$ · M$^{-1}$ | k$_{cat}$ s$^{-1}$ | K$_M$ µM | k$_{cat}$/K$_M$ × 10$^5$ s$^{-1}$ · M$^{-1}$ | detection method |
| NADPH | PobA | — | — | — | 54 ± 5 | 18 ± 2 | 30 ± 4 | 50 ± 5 | 43 ± 3 | 12 ± 1 | NADPH$^e$ |
| | | 53 ± 5 | 70 ± 5 | 7.6 ± 0.7 | 40 ± 4 | 21 ± 1 | 19 ± 2 | 47 ± 4 | 66 ± 6 | 7.1 ± 0.7 | O$_2$$^f$ |
| | PraI | — | — | — | 27 ± 3 | 16 ± 1 | 17 ± 2 | 27 ± 2 | 27 ± 1 | 10 ± 1 | NADPH |
| | | 25 ± 2 | 68 ± 6 | 3.7 ± 0.3 | 23 ± 2 | 19 ± 2 | 19 ± 2 | 23 ± 2 | 33 ± 2 | 6.9 ± 0.7 | O$_2$ |
| NADH | | — | — | — | 26 ± 2 | 18 ± 1 | 14 ± 1 | 25 ± 2 | 49 ± 3 | 5.1 ± 0.5 | NADH |
| | | 22 ± 2 | 54 ± 5 | 4.0 ± 0.4 | 21 ± 2 | 16 ± 1 | 13 ± 1 | 22 ± 2 | 46 ± 4 | 4.8 ± 0.6 | O$_2$ |

$^a$Experiments were performed using 50 mM Tris/SO4, pH 8 supplemented with 60 µM FAD, at 25° C. Parameters were calculated using a minimum of 25 data points.
$^b$Experiments were performed using 200 µM 4-hydroxybenzoate and 300 µM NAD(P)H.
$^c$Experiments were performed using air-saturated buffer and 300 µM NAD(P)H.
$^d$Experiments were performed using air-saturated buffer and 200 µM 4-hydroxybenzoate.
$^e$Measurements were performed spectrophotometrically by monitoring the loss of NAD(P)H signal at 340 nm.
$^f$Measurements were performed using an oxygraph by following the depletion of O$_2$.

Without being limited by theory, in an embodiment, a PobA-bearing strain may not exhibit optimal engineered properties. In a possible first interpretation, the PobA is likely not performing at top speed due to the limited NADPH concentration as indicated by the whole cell NADPH measurements. Competing NADPH consumption for anabolic processes and PobA activity. In a possible second interpretation, the strong constitutive promoter for praI results in a higher effective protein concentration which compensates for lowered activity. In an embodiment, turn-over number for PobA is double that of PraI.

In another embodiment, attempts are made at swapping NAD(P)H preferences. K$_m$ values typically reflect the intracellular level of the metabolite to ensure a responsive enzyme system towards the changing environments, substrates and solutions. Without being limited by theory, affinity towards oxygen or 4HB are unlikely to affect the strain's productivity.

In a prophetic embodiment, assisted laboratory evolution experiments will create engineered *Pseudomonas* with improved properties disclosed herein.

Thus, disclosed herein are compositions of matter and methods useful to overcome a key bottleneck in the rate of 4-HBA conversion to the central intermediate, PCA, which can either be ring-opened directly, or as disclosed herein, decarboxylated to catechol and ring-opened to MA. By addressing this bottleneck, we have improved the titer to 40 g/L MA at 100% molar yield using pCA as feed. Without being limited by theory, we anticipate that the replacement of pobA with praI will also confer rate enhancements in strains that produce compounds via ring-opening with PCA or NADPH-intensive target products. In a prophetic embodiment, it is contemplated to increase the complexity of the feedstock input starting from a defined aromatic mixture to Cultures were grown in the presence of 20 mM (3.26 g/L) p-coumarate and 10 mM glucose, and the 12-hour time point was quantified.

Plasmid construction. We used Q5® Hot Start High-Fidelity 2× Master Mix (New England Biolabs) for all polymerase chain reactions (PCR). NEBUILDER® HiFi DNA Assembly Master Mix (New England Biolabs) was used to assemble plasmids, followed by transformation into NEB 5-alpha FI$^q$ competent *E. coli* cells (New England Biolabs). All plasmids were confirmed by Sanger sequencing (GENEWIZ).

Strain construction. Competent *P. putida* cells were prepared following procedures known in the art. Plasmid DNA (300-500 ng) was transformed into competent *P. putida* cells (50 uL) using electroporation methods. Cells were recovered in 950 uL SOC for 1-2 hours at 30° C., 225 rpm. Following the recovery period, the culture was transferred to LB kan50 agar plates to select for correctly integrated plasmids. Counterselection using 25% sucrose confirmed loss of the plasmid as previously described. We used MYTAQ™ HS Red Mix (Bioline) for colony PCR reactions to confirm gene replacements.

BioscreenC and shake flask cultivations. Shake flask experiments were conducted with modified M9 minimal media (insert recipe here) supplemented with 20 mM (3.26 g/L) p-coumarate and 10 mM glucose (1.80 g/L). Optical density (OD$_{600}$) of cultures was measured at 600 nm using Beckman DU640 spectrophotometer (BECKMAN COULTER®). *P. putida* strains were inoculated overnight in 5 mL of LB medium. The overnight culture was inoculated into 25 mL media in 125 mL baffled flasks at OD$_{600}$ 0.10 nm and grown at 30° C., 225 rpm for 72 hours.

Protein expression and production. The genes for pobA (PP_3537) and praI (BAH79107) were amplified from synthetic constructs pEUK005 or pEUK006 (TWIST Bioscience) codon optimized for *Escherichia coli*, and cloned into a pET-21b(+) backbone using Gibson assembly master mix (New England Biolabs) to produce pEUK018 and pEUK019, which encode for tagless PobA and PraI, respectively. Alternatively, a praI over-expression construct was made using HiFi Assembly protocol (NEB) to include a C'-polyHis tag (PraI-His) in pET-21b(+) backbone (pEE003). PobA was heterologously produced in *E. coli* BL-21 λ(DE3) grown on lysogeny broth (LB) media containing ampicillin (100 mg/L); PraI was produced in *E. coli* Lemo-21 λ(DE3) grown on terrific broth (TB) containing ampicillin (100 mg/L) and chloramphenicol (30 mg/L). The starter cultures were grown from a single colony of *E. coli* transformed with an appropriate plasmid (or an equivalent glycerol stock) were grown overnight in LB with the appropriate antibiotics. 10 mL of the starter culture was used to inoculate a 4 L baffled flask containing 1 L of LB (PobA) or TB (PraI) with antibiotics and grown at 37° C., 225 rpm. The cultures were induced at an $OD_{600}$ of ~0.7 with 1 mM IPTG and 0.2 mM of riboflavin; additionally, 1 mg/mL of biotin was added to cultures producing PraI. Subsequently, the cultures were grown for an additional 16-18 hr at 20° C., 225 rpm. The resulting biomass was collected by centrifugation and frozen at –80° C. until further use. Tagless PobA and PraI were used for kinetic analyses and the PraI-His was used for protein crystallography. For purification, thawed biomass was suspended in an equivalent volume of 20 mM HEPES, 100 mM NaCl, pH 7.5 containing a trace amount of DNAseI, and lysed by sonication. The cell lysate was cleared by centrifugation and passage through 0.45-micron filter. Tagless PobA and PraI were purified using the combinations of $(NH_4)_2SO_4$ precipitation, hydrophobic interaction chromatography, and anion exchange chromatography. The chromatographic purification of PobA and PraI was assisted by the yellow coloration of their flavin cofactor and was performed using an AKTA PURE™ FPLC system (Cytiva) using 20 mM HEPES, 100 mM NaCl, pH 7.5 as the buffer A. 1 M $(NH_4)_2SO_4$ was added to the cleared lysates, and the precipitated proteins were removed by centrifugation. The soluble protein fraction was injected to a Source-15 Phenyl (Cytiva) with a gradient of 1-0 M $(NH_4)_2SO_4$ in 120 mL. Fractions containing PobA or PraI were pooled, dialyzed into buffer A, and injected to a Source-15 Q (Cytiva) with a gradient of 0.1-0.5 M NaCl in 60 mL. Fractions containing PobA or PraI were pooled, dialyzed into buffer A, frozen as beads in liquid $N_2$, and stored at –80° C.

PraI-His Purification

Steady-state kinetic analysis. The hydroxylation of 4-hydroxybenzoate was monitored continuously by following the consumption of the co-substrates NAD(P)H or $O_2$. NAD(P)H consumption was monitored using a Cary 4000 UV-Vis spectrophotometer (Agilent) connected to a peltier device at 340 nM ($\varepsilon_{340}$=6 $mM^{-1}$ $cm^{-1}$); $O_2$ consumption was monitored using a Clark-type electrode oxygraph OXYG1+ (Hansatech) connected to a circulating water bath and calibrated using air-saturated water and $Na_2S_2O_4$ according to the manufacturer's instruction. The standard assay was performed in air-saturated 50 mM Tris/$SO_4$ pH 8 supplemented with 60 M FAD at 25° C. and initiated by the addition of 20 nM of PobA or PraI. Initial velocities were measured as a function of the NAD(P)H, 4-hydroxybenzoate, or $O_2$ concentrations. 300 M of NAD(P)H and 200 M of 4-hydroxybenzoate were used when varying the $O_2$ concentration, and when varying the 4-hydroxybenzoate or NAD(P)H concentrations. NAD(P)H consumption assays were used when varying the concentrations of 4-hydroxybenzoate or NAD(P)H; and $O_2$ consumption assays were used when individually varying the concentrations of all three substrates. Different starting $O_2$ concentrations were achieved by bubbling $N_2$ gas into the buffer prior to sealing the oxygraph chamber and initiating the reaction. The initial $O_2$ concentrations were normalized to the ambient air-saturated buffer in between runs. The steady-state kinetic parameters were obtained by fitting the Michaelis-Menten equation to the data using LEONORA.

Reaction Stoichiometry

Molar balances of the reactants and products in the PHBH-catalyzed reactions were evaluated using the combination of oxygraph, spectrophotometer, and HPLC-based assays. An end-point assay was performed in air-saturated 50 mM Tris/$SO_4$ pH 8 supplemented with 60 M FAD, where the mixture also contained 100 μM 4HB, 300 M NAD(P)H, and the reaction was initiated by the addition of 1 M PobA or PraI. The reaction was let to completion by the depletion of 4HB and the total $O_2$ consumed during this process was monitored in an oxygraph. Subsequently, the amount of remaining NAD(P)H in the completed reaction was monitored spectrophotometrically. Finally, the concentration of PCA produced was monitored on an HPLC. A control with acid inactivated enzymes was included for evaluating the starting 4HB amount. The data was reported as an average of three independent replicates.

TABLE 2

| Plasmids used herein | | |
| --- | --- | --- |
| Plasmid | Utility | Construction details |
| pCJ041 | Vector for deletion of pobAR in *P. putida* KT2440-derived strains | Previously described |
| pCJ107 | Vector for integration of Ptac:vanAB downstream of fpvA in *P. putida* KT2440-derived strains | Previously described |
| pCJ128 | Vector for integration of Ptac:pobA:vanAB 5' of fpvA in *P. putida* KT2440-derived strains | pobA was amplified from *P. putida* KT2440 genomic DNA using primers oCJ629/oCJ631 and the product was assembled with pCJ107 digested with XbaI. |
| pCJ174 | Vector for replacement of fpvA with praI:vanAB in *P. putida* KT2440-derived strains | The praI gene from *Paenibacillus* sp. JJ-1b was synthesized as a gBlock by IDT. The gBlock was assembled with pCJ128 digested with BamHI and EagI. |

TABLE 2-continued

Plasmids used herein

| Plasmid | Utility | Construction details |
|---|---|---|
| pEE003 | T7-inducible expression construct to produce a codon optimized His-tagged PraI in E. coli | pET-21b(+) expression vector containing praI gene fragment (gblock EE_PraI_Pae_opt_Ec; optimized for E. coli K12 MG1665 expression) between insertion points: NdeI and XhoI and assembled by a HiFi Assembly protocol (NEB) to produce pEE003. The sequence fidelity was confirmed by sequencing using T7_fwd and T7_rev (Genewiz). |
| pEUK005 | synthetic praI construct codon optimized for E. coli | The synthetic pobA gene was codon optimized fr E. coli expression (PP_3537, named pobA_EC, Table S3) and cloned into the plasmid pET-29a(+) by TWIST Bioscience. |
| pEUK006 | synthetic praI construct codon optimized for E. coli | The synthetic praI gene was codon optimized for E. coli expression (BAH79107, named praI_EC, Table S3) and cloned into the plasmid pET-29a(+) by TWIST Bioscience. |
| pEUK018 | T7-inducible expression construct to produce a codon optimized tagless PobA in E. coli | The pobA gene was amplified from pEUK005 by oEUK030 and oEUK031 (Table S2) using Phusion polymerase (NEB). The PCR product was subcloned to pET-21b(+) between NdeI and BamHI using a Gibson assembly master mix (NEB). The resulting plasmid was sequence confirmed with T7_fwd and T7_rev (Genewiz) and transformed into E. coli BL-21 λ(DE3) and to generate EUK047 (Table S4). |
| pEUK019 | T7-inducible expression construct to produce a codon optimized tagless PraI in E. coli | The praI gene was amplified from pEUK006 by oEUK032 and oEUK033 (Table S2) using Phusion polymerase (NEB). The PCR product was subcloned to pET-21b(+) between NdeI and BamHI using a Gibson assembly master mix (NEB). The resulting plasmid was sequence confirmed with T7_fwd and T7_rev (Genewiz) and transformed into E. coli Lemo-21 λ(DE3) and to generate EUK045 |

TABLE 3

DNA Sequences of oligos used herein.

| Primer | Sequence (5' to 3') | Description |
|---|---|---|
| oCJ055 | TCCGCTCACAATTCCACAC | Diagnostic: binds to Ptac promoter reverse |
| oCJ288 | CTAGCTTCACGCTGCCGCAAG | pK18mobsacB linear forward |
| oCJ289 | CTAACTCACATTAATTGCGTTGCGCTCACTG | pK18mobsacB linear reverse |
| oCJ292 | AGTGAGCGCAACGCAATTAATGTGAGTTAGCGAACT TTAGTAAAGGCTGGGCTTTCAGTTCATC | pobA upstream targeting region forward with pK18mobsacB overlap |
| oCJ293 | GCGGCCGCGGGCTGCGAGCTACGGG | pobA upstream targeting region reverse with NotI site |
| oCJ296 | CCTGACCCGTAGCTCGCAGCCCGCGGCCGCGTGTGG ATCAGCCGCCGTC | pobR downstream targeting region forward with upstream targeting region overlap |
| oCJ297 | CCCTGAGTGCTTGCGGCAGCGTGAAGCTAGGCCCGC TTCGGTAAGGTCG | pobR downstream targeting region reverse with pK18mobsacB overlap |
| oCJ298 | ACCTTTCATCTGCGGACC | Diagnostic: Outside pobA upstream targeting region forward |
| oCJ299 | ATCTGTGGCACCCACTTG | Sequencing: Outside pobR downstream targeting region reverse |
| oCJ311 | AGCCTCTTCAGCGTCAAC | Diagnostic: Outside fpvA upstream targeting region forward |

TABLE 3-continued

DNA Sequences of oligos used herein.

| Primer | Sequence (5' to 3') | Description |
|---|---|---|
| oCJ312 | CACGCCTGCTTCATTGAAC | Diagnostic: Outside fpvA downstream targeting region reverse |
| oCJ550 | TGCACCTGTATGTATGCG | Diagnostic: vanB forward |
| oCJ629 | TGGAATTGTGAGCGGATAACAATTTCACACTCTAGA AAAGAAGGTAGTTATGAAAACTCAGGTTGCAATTA TTGGTGCAGG | PobA forward with synthetic Salis RBS with XbaI site and tac promoter overlap |
| oCJ631 | GGCGACGTACCAGGTGTTTTTGGGGTACATGGGTGG CTCTCCTCATATGTCAGGCAACTTCCTCGAACGGC | pobA reverse with Salis RBS and vanAB overlap |
| oEUK030 | AGAAGGAGATATACATATGAAGACGCAGGTTG | Forward primer used to subclone praI in the construction of pEUK018. |
| oEUK031 | AGCTCGAATTCGGATCCTCAGGCCACTTCTTCG | Reverse primer used to subclone praI in the construction of pEUK018. |
| oEUK032 | AGAAGGAGATATACATATGCGCACTCAGGTA | Forward primer used to subclone praI in the construction of pEUK019. |
| oEUK033 | GCTCGAATTCGGATCCTCAAAACTCCATCGGC | Reverse primer used to subclone praI in the construction of pEUK019. |
| T7_fwd | TAATACGACTCACTATAGGG | sequencing primer |
| T7_rev | GCTAGTTATTGCTCAGCGG | sequencing primer |

TABLE 4

Synthesized genes disclosed herein.

| Name | Sequence (5' to 3') | Description |
|---|---|---|
| pobA_EC | ATGAAGACGCAGGTTGCAATTATCGGCGCAGGTCCGAGCGGCCT CCTTCTGGGTCAATTGCTGCATAAAGCGGGCATTGATAATATTAT TGTGGAACGCCAGACTGCGGAATATGTCCTGGGCCGCATCCGTG CAGGTGTGCTGGAGCAGGGTACCGTGGATCTGCTGCGGGAAGCG GGTGTAGCGGAACGCATGGATCGGGAAGGGTTAGTGCACGAAG GGGTAGAGCTGCTGGTGGGCGGACGTCGTCAGCGTCTCGACCTG AAAGCGCTGACTGGAGGCAAGACGGTCATGGTCTATGGTCAAAC GGAGGTCACCCGCGATCTGATGCAGGCCCGCGAAGCATCAGGTG CGCCGATCATCTACAGCGCGGCAAACGTTCAGCCACACGAGCTG AAGGGAGAAAAGCCATACTTGACGTTCGAAAAAGATGGTCGCG TCCAGCGCATTGATTGCGATTATATTGCGGGATGCGATGGCTTCC ATGGTATCTCGCGTCAGAGTATCCCGGAAGGTGTTCTGAAGCAG TATGAGCGTGTCTATCCGTTTGGTTGGTTGGGGCTGTTAAGCGAC ACACCGCCCGTTAACCATGAACTGATCTACGCACACCATGAACG CGGTTTCGCTCTTTGCAGCCAGCGTTCGCAGACCCGTTCACGCTA CTACCTGCAGGTCCCATTGCAGGATCGTGTTGAAGAATGGTCCG ACGAACGTTTCTGGGATGAATTGAAAGCCCGCCTGCCTGCCGGAA GTTGCGGCGGACCTGGTTACGGGACCGGCGTTGGAAAAAAGCAT TGCCCCATTGCGCAGCCTGGTGGTGGAACCAATGCAGTACGGTC ACCTGTTCTTAGTGGGTGATGCGGCGCACATTGTGCCGCCGACC GGCGCCAAAGGCCTGAATCTGGCCGCGAGCGATGTTAATTATCT GTATCGTATTCTGGTTAAAGTTTACCACGAAGGTCGGGTGGACC TGTTGGCCCAGTATAGCCCGCTGGCGCTGCGCCGCGTGTGGAAA GGAGAACGTTTTAGCTGGTTCATGACGCAACTTTTACACGACTTT GGGAGCCATAAAGATGCGTGGGATCAGAAGATGCAGGAAGCCG ACCGGGAGTATTTTCTGACGTCGCCGGCGGGTCTGGTGAACATT GCTGAAAACTACGTTGGCTTACCGTTCGAAGAAGTGGCCTGA | (SEQ ID NO: 1) The pobA (PP_3537) sequence from *P. putida* KT2440 codon optimized for expression in *E. coli* used for the constructions of pEUK005 and pEUK018. |
| EE_PraI_Pae_opt_Ec | CGCACCCAGGTTGGTATCATTGGCGCGGGTCCGGCCGGTCTGTT GCTGTCCCACTTGCTGTACCTGCAGGGCATCGAAAGCATCATCA TCGAAAACCGTACCCGTGAGGAAATCGAAGGTACGATTCGTGCC GGTGTACTGGAACAGGGCACCGTTGATCTGATGAATCAGATGGG GGTGGGCGCGCGTATGATGAAGGAGGGGCCACTTCCACGAAGGTT TCGAACTGCGCTTCAACGGTCGTGGCCACCGTATCAACGTACAC | (SEQ ID NO: 2) The praI (BAH79107) sequence from *Paenibacillus* JJ-1b codon optimized for expression in *E. coli* |

TABLE 4-continued

| Synthesized genes disclosed herein. | | |
|---|---|---|
| Name | Sequence (5' to 3') | Description |
|  | GAGCTGACCGGTGGTAAATACGTCACGGTTTATGCCCAGCACGA AGTTATTAAAGACCTCGTGGCTGCACGTCTGCAAACAGGTGGTC AGATTCATTTTAACGTAGGTGACGTTAGCCTGCACGACGTTGAT ACCAGCTCTCCGAAAATCCGTTTTCGCCCGAACAAAGACGGTGA GCTGCAGGAGATTGAATGCGACTTCATCGCGGGTTGCGATGGTT TCCGTGGCCCGTCACGCCCGGCAATCCCACAGTCCGTACGTAAA GAATACCAAAAAGTGTATCCTTTCAGCTGGCTGGGCATCCTCGT GGAGGCGCCGCCGTCCGCTCACGAACTGATCTACGCGAACCATG AACGTGGTTTTGCACTGGTGAGTACCCGCTCACCGCAGATTCAG CGTCTGTACCTGCAGGTAGACGCGCAGGATCATATTGACAACTG GTCTGATGACCGTATCTGGAGCGAACTCCACGCGCGCCTGGAAA CTCGTGATGGTTTCAAACTGCTGGAAGGCCCGATCTTCCAAAAG GGTATCGTTTCCATGCGCAGCTTCGTATGTGATCCAATGCAGCAC GGTCGCCTGTTCCTAGCAGGTGATGCGGCGCACATCGTACCGCC GACCGGCGCCAAAGGTCTGAACCTGGCAGCGGCCGACGTTCAG GTCCTGGCCCGTGGTTTAGAAGCATATTACAAAGCTGGCAAAAT GGAAATTCTGAACCGCTGCACCGAAATTTGCCTCCGTCGTATCT GGAAAGCCGAACGCTTCAGCTGGTTCATGACTACTATGCTCCAC CGTGACCAGGGCCATACTCCGTTCGAACGCGGTATCCAACTGGC AGAGCTGGACTATGTTACCTCTTCTCGTGCCGCGTCAACCAGCCT GGCTGAAAACTATATTGGCCTGCCGATGGAGTTC | used for the construction of pEE003. |
| praI_EC | ATGCGCACTCAGGTAGGCATTATTGGGGCCGGTCCGGCTGGGTT GCTGTTGTCACATTTGTTATATTTGCAAGGGATCGAAAGCATCAT TATTGAGAACCGTACGCGTGAGGAGATTGAGGGTACCATTCGCG CAGGTGTGTTAGAACAGGGCACGGTGGATCTGATGAATCAAATG GGTGTGGGTGCCCGTATGATGAAAGAAGGCCACTTCCACGAAGG GTTTGAGCTCCGTTTTAACGGCCGCGGGCATCGTATCAATGTGC ACGAGCTGACGGGTGGCAAATACGTTACGGTGTACGCGCAACAT GAGGTTATCAAAGATCTGGTTGCGGCGCGCCTGCAGACCGGCGG GCAAATTCATTTTAACGTTGGTGACGTAAGCTTACACGACGTCG ATACCTCTAGCCCGAAAATTCGTTTTCGTCCCAATAAAGATGGC GAACTGCAAGAAATTGAGTGCGACTTCATCGCCGGTTGCGACGG CTTTCGCGGGCCGTCTCGCCCGGCAATCCCGCAGAGTGTACGTA AAGAATATCAGAAGGTTTATCCTTTTAGCTGGTTAGGCATTCTGG TCGAAGCGCCGCCTTCTGCGCATGAACTTATTTATGCAAATCATG AGCGGGGTTTTGCACTGGTGTCGACGCGCTCACCGCAAATTCAA CGGCTTTACTTACAGGTGGACGCCCAAGATCATATCGACAACTG GAGCGACGACCGCATCTGGAGTGAATTGCACGCGCGCCTTGAAA CTCGGGACGGCTTCAAGCTGCTGGAGGGACCGATCTTTCAAAAA GGTATTGTTTCCATGCGGTCATTTGTGTGCGATCCGATGCAACAT GGTCGTTTATTTCTGGCTGGCGATGCTGCCCATATCGTGCCCCCG ACTGGGGCGAAAGGTCTTAACCTGGCCGCTGCAGACGTCCAAGT CCTTGCGCGTGGCCTGGAAGCGTATTATAAAGCCGGCAAGATGG AAATTCTGAACCGTTGCACCGAAATCTGCTTACGCCGCATCTGG AAGGCTGAGCGCTTTAGTTGGTTCATGACTACCATGCTGCATCG CGATCAGGGACACACCCCTTTCGAACGTGGTATCCAGCTCGCGG AACTGGATTACGTAACCTCTTCGCGCGCGGCGTCGACGAGCCTC GCCGAAAACTATATCGGCTTGCCGATGGAGTTTTGA | (SEQ ID NO: 3) The praI (BAH79107) sequence from Paenibacillus JJ-1b codon optimized for expression in E. coli used for the constructions of pEUK006 and pEUK019. |

TABLE 5

| Strains and construction details for bacterial strains disclosed herein. | | |
|---|---|---|
| Strain | Genotype | Construction details |
| CJ242 | P. putida KT2440 ΔcatRBCA::Ptac:catA ΔpcaHG::Ptac:aroY:ecdBD Δcrc | Previously described |
| CJ680 | P. putida KT2440 ΔcatRBCA::Ptac:catA ΔpcaHG::Ptac:aroY:ecdBD Δcrc ΔfpvA::Ptac::praI:vanAB | fpvA was replaced with Ptac:praI:vanAB by transforming CJ242 with pCJ174. After sucrose selection the replacement of fpvA with Ptac:praI:vanAB was confirmed by amplification of a 5458 bp fragment using primers oCJ311/oCJ312 Integration of the plasmid at the correct locus was confirmed after the fact. |
| CJ750 | P. putida KT2440 ΔcatRBCA::Ptac:catA ΔpcaHG::Ptac:aroY:ecdBD; Δcrc ΔpobAR | pobAR was deleted from CJ242 by transforming CJ242 with pCJ041. After sucrose selection, the deletion of pobAR was confirmed by amplification of a 2094 bp band using primers oCJ298/oCJ299. |
| CJ781 | P. putida KT2440 ΔcatRBCA::Ptac:catA | fpvA was replaced with Ptac:praI:vanAB by transforming CJ750 with pCJ174. Integration at the correct locus was confirmed using primer |

TABLE 5-continued

| | Strains and construction details for bacterial strains disclosed herein. | |
|---|---|---|
| Strain | Genotype | Construction details |
| | ΔpcaHG::Ptac:aroY:ecdBD Δcrc ΔpobAR ΔfpvA::Ptac:praI:vanAB | pair oCJ311/oCJ055 for the upstream region and oCJ312/oCJ550 for downstream region with respect to fpvA. After sucrose selection. The correct integration of praI was confirmed by amplification of a . . . bp band using oCJ311/oCJ312. |
| EUK045 | E. coli Lemo-21 λ(DE3) | E. coli Lemo-21 λ(DE3) transformed with pEUK019. |
| EUK044 | E. coli Lemo-21 λ(DE3) | E. coli Lemo-21 λ(DE3) transformed with pEE003. |
| EUK047 | E. coli BL-21 λ(DE3) | E. coli BL-21 λ(DE3) transformed with pEUK018. |

Stoichiometry of PHBH-Catalyzed Reaction.

The reaction was performed in air-saturated buffer using 0.2 µM PobA or PraI, 100 µM 4-HBA, 300 µM NAD(P)H. Total oxygen concentration consumed was assessed using an oxygraph. Total protocatechuate produced was measured using HPLC-based assay using authentic protocatechuate standard. The measurements listed in Table 6 were an average of three independent readings and the error represent the standard deviation.

TABLE 6

| | | Stoichiometry of PHBH-catalyzed reaction. | |
|---|---|---|---|
| Enzyme | Nicotinamide cofactor | $O_2$ consumed per 4-HBA consumed (mol/mol) | PCA produced per4-HBA consumed (mol/mol) [b] |
| PobA | NADPH | 1.01 ± 0.04 | 1.12 ± 0.03 |
| PraI | NADPH | 1.07 ± 0.01 | 0.98 ± 0.02 |
| PraI | NADH | 1.03 ± 0.05 | 1.18 ± 0.06 |

The foregoing discussion and examples have been presented for purposes of illustration and description. The foregoing is not intended to limit the aspects, embodiments, or configurations to the form or forms disclosed herein. In the foregoing Detailed Description for example, various features of the aspects, embodiments, or configurations are grouped together in one or more embodiments, configurations, or aspects for the purpose of streamlining the disclosure. The features of the aspects, embodiments, or configurations, may be combined in alternate aspects, embodiments, or configurations other than those discussed above. This method of disclosure is not to be interpreted as reflecting an intention that the aspects, embodiments, or configurations require more features than are expressly recited in each claim. Rather, as the following claims reflect, inventive aspects lie in less than all features of a single foregoing disclosed embodiment, configuration, or aspect. While certain aspects of conventional technology have been discussed to facilitate disclosure of some embodiments of the present invention, the Applicants in no way disclaim these technical aspects, and it is contemplated that the claimed invention may encompass one or more of the conventional technical aspects discussed herein. The following claims are hereby incorporated into this Detailed Description, with each claim standing on its own as a separate aspect, embodiment, or configuration.

What is claimed is:

1. An engineered *Pseudomonas* bacterium comprising a gene encoding an exogenous PraI, wherein the bacterium is free of a gene encoding an endogenous PobA and wherein the bacterium increases production of muconic acid from p-coumarate when compared to a non-engineered *Pseudomonas* bacterium that comprises a gene encoding an endogenous PobA and wherein the bacterium produces at least 40 g/L of muconic acid; and wherein the gene encoding for PraI is greater than 85% identical to SEQ ID NO: 3; and wherein the bacterium has increased production of beta-ketoadipic acid when compared to a non-engineered *Pseudomonas* bacterium that comprises a gene encoding endogenous PobA.

2. The engineered *Pseudomonas* bacterium of claim 1, wherein the *Pseudomonas* bacterium is *Pseudomonas* strain CJ781.

3. An engineered *Pseudomonas* bacterium comprising a gene encoding an exogenous PraI, wherein the bacterium is free of a gene encoding an endogenous PobA and is free of a gene encoding an endogenous PcaIJ and wherein the bacterium increases production of muconic acid from p-coumarate when compared to a non-engineered *Pseudomonas* bacterium that comprises a gene encoding an endogenous PobA and a gene encoding an endogenous PcaIJ and wherein the bacterium produces at least 40 g/L of muconic acid; and wherein the gene encoding for PraI is greater than 85% identical to SEQ ID NO: 3; and wherein the bacterium has increased production of beta-ketoadipic acid when compared to a non-engineered *Pseudomonas* bacterium that comprises a gene encoding endogenous PobA and a gene encoding endogenous PcaIJ and is free of a gene encoding exogenous PraI.

4. The engineered *Pseudomonas* bacterium of claim 3, wherein the *Pseudomonas* is *Pseudomonas* strain AW271.

*   *   *   *   *